(12) United States Patent
Kirkpatrick et al.

(10) Patent No.: US 6,480,743 B1
(45) Date of Patent: Nov. 12, 2002

(54) SYSTEM AND METHOD FOR ADAPTIVE BRAIN STIMULATION

(75) Inventors: Bruce Kirkpatrick; Benjamin D. Pless, both of Sunnyvale, CA (US)

(73) Assignee: NeuroPace, Inc., Sunnyvale, CA (US)

( * ) Notice: Subject to any disclaimer, the term of this patent is extended or adjusted under 35 U.S.C. 154(b) by 0 days.

(21) Appl. No.: 09/962,940

(22) Filed: Sep. 24, 2001

Related U.S. Application Data

(63) Continuation-in-part of application No. 09/543,264, filed on Apr. 5, 2000, and a continuation-in-part of application No. 09/543,450, filed on Apr. 5, 2000.

(51) Int. Cl.[7] .................................................. A61N 1/36
(52) U.S. Cl. ....................................................... 607/45
(58) Field of Search ............................ 607/45; 600/544, 600/545

(56) References Cited

U.S. PATENT DOCUMENTS 5,025,807 A  *  6/1991  Zabara
6,016,449 A  *  1/2000  Fischell et al.

* cited by examiner

*Primary Examiner*—Scott M. Getzow

(57) ABSTRACT

An implantable neurostimulator adapted to provide adaptive electrical brain stimulation includes a detection subsystem for isolating an electrographic signal characteristic and a stimulation system for applying an adaptive stimulation signal based at least in part upon the electrographic signal characteristic and correlated with the electrographic signal. Undesired learning of and acclimation to stimulation characteristics are avoided and stimulation efficacy is improved by adapting or otherwise varying the adaptive stimulation signal in relation to the electrographic signal.

23 Claims, 14 Drawing Sheets

SYSTEM AND METHOD FOR ADAPTIVE BRAIN STIMULATION

CROSS-REFERENCE TO RELATED APPLICATIONS

This is a continuation-in-part of U.S. patent application Ser. Nos. 09/543,264 and 09/543,450, both filed on Apr. 5, 2000.

FIELD OF THE INVENTION

The invention relates to electrical stimulation therapy for neurological disorders, and more particularly to a system and method for adapting stimulation waveforms to a measured characteristic of an electrographic signal received from the patient's brain.

BACKGROUND OF THE INVENTION

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenytoin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20–30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide clinical benefit. The Activa device from Medtronic is a pectorally implanted continuous deep brain stimulator intended primarily to treat Parkinson's disease; it has also been tested for epilepsy. In operation, it supplies a continuous electrical pulse stream to a selected deep brain structure where an electrode has been implanted.

Continuous stimulation of deep brain structures for the treatment of epilepsy has not met with consistent success. To be effective in terminating seizures, it is believed that one effective site where stimulation should be performed is near the focus of the epileptogenic region of the brain. The focus is often in the neocortex, where continuous stimulation may cause significant neurological deficit with clinical symptoms including loss of speech, sensory disorders, or involuntary motion. Accordingly, research has been directed toward automatic responsive epilepsy treatment based on a detection of imminent seizure.

The episodic attacks or seizures experienced by a typical epilepsy patient are characterized by periods of abnormal neurological activity. "Epileptiform" activity refers to specific neurological activity associated with epilepsy as well as with an epileptic seizure and its precursors; such activity is frequently manifested in electrographic signals in the patient's brain.

Most prior work on the detection and responsive treatment of seizures via electrical stimulation has focused on analysis of electroencephalogram (EEG) and electrocorticogram (ECoG) waveforms. In general, EEG signals represent aggregate neuronal activity potentials detectable via electrodes applied to a patient's scalp, and ECoGs use internal electrodes near the surface of or within the brain. ECoG signals, deep-brain counterparts to EEG signals, are detectable via electrodes implanted on the dura mater, under the dura mater, or via depth electrodes (and the like) within the patient's brain. Unless the context clearly and expressly indicates otherwise, the term "EEG" shall be used generically herein to refer to both EEG and ECoG signals.

It is generally preferable to be able to detect and treat a seizure at or near its beginning, or even before it begins. The beginning of a seizure is referred to herein as an "onset."However, it is important to note that there are two general varieties of seizure onsets. A "clinical onset" represents the beginning of a seizure as manifested through observable clinical symptoms, such as involuntary muscle movements or neurophysiological effects such as lack of responsiveness. An "electrographic onset" refers to the beginning of detectable electrographic activity indicative of a seizure. An electrographic onset will frequently occur before the corresponding clinical onset, enabling intervention before the patient suffers symptoms, but that is not always the case. In addition, there often are perceptible changes in the EEG, or "precursors," that occur seconds or even minutes before the electrographic onset that can be identified and used to facilitate intervention before electrographic or clinical onsets occur. This capability would be considered seizure prediction, in contrast to the detection of a seizure or its onset.

It has been suggested that it is possible to treat and terminate seizures by applying specific responsive electrical stimulation signals to the brain. See, e.g., U.S. Pat. No. 6,016,449 to Fischell et al., H. R. Wagner, et al., Suppression of cortical epileptiform activity by generalized and localized ECoG desynchronization, Electroencephalogr. Clin. Neurophysiol. 1975; 39(5): 499–506; and R. P. Lesser et al., Brief bursts of pulse stimulation terminate after discharges caused by cortical stimulation, Neurology 1999; 53 (December): 2073–81 . Unlike the continuous stimulation approaches described above, responsive stimulation is intended to be performed only when a seizure (or other undesired neurological event) is occurring or about to occur. This approach is believed to be preferable to continuous or semi-continuous stimulation, as stimulation at inappropriate times and quantities may result in the initiation of seizures, an increased susceptibility to seizures, or other undesired side effects.

While responsive stimulation alone is considered an advantageous therapy for seizures, it is believed possible to further reduce the incidence of seizures by applying continuous or periodic scheduled stimulation to certain parts of the brain while also performing responsive electrical stimulation as described above. See, for example, U.S. patent application Ser. No. 09/543,450 filed on Apr. 5, 2000; U.S. Pat. No. 5,683,422 to Rise; and I. S. Cooper et al., "Effects of Cerebellar Stimulation on Epilepsy, the EEG and Cerebral Palsy in Man,"Electroencephalogr. Clin. Neurophysiol. 1978; 34: 349–54.

Some have long recognized that "seizures may beget more seizures" E. H. Reynolds, "The Process of Epilepsy" in T. G. Bolwig et al., ed., *The Clinical Relevance of Kindling*, ch. 10, p. 149 (Chichester, England: John Wiley & Sons 1989), citing W. R. Gowers, *Epilepsy and Other Chronic Convulsive Diseases* (London: Churchill 1881 ). Accordingly, an advantage of a device or other treatment that is able to terminate, avoid, or inhibit seizures is that the continued progression of a disease such as otherwise intractable epilepsy may be avoided.

However, there is a need to avoid excess, improper, or regularly repeated stimulation, which may be particularly acute and important in some circumstances, as the central nervous system has a tendency to learn and acclimate to new conditions and stimuli.

As regularly repeated seizures appear to alter the anatomic substrate of the brain (i.e., the neuronal connections, characteristics, and conditions that tend to define the brain's function), so apparently do "suitably spaced successive subclinical stimuli" (Reynolds, 1989)—and so might certain predictable and learnable patterns of artificially introduced electrical stimulation that are actually intended to terminate, avoid, or inhibit epileptiform activity. In other words, under certain circumstances, regularly repeated electrical stimulation might eventually result in an increased susceptibility to seizures or other undesired activity, particularly when such stimulation occurs in combination with (or can be associated with) seizures or subclinical activity.

These effects might be attributable to brain mechanisms identical or similar to those involved in learning. See, e.g., E. R. Kandel, "Cellular Mechanisms of Learning and the Biological Basis of Individuality" in Kandel et al., ed., *Principles of Neural Science*, 3d ed., ch. 65, pp. 1009–24 (Norwalk, Conn.: Appleton & Lange 1991 ). Relatively short-term and small-scale (neuronal level) learning effects (such as habituation, a form of non-associative learning in which an evoked physiological response decreases continually with repetitive application of the same stimulus) may play a part in this, but there is evidence to support the involvement of more complex long-term memory forming mechanisms, such as long-term potentiation (LTP). Kindling, an experimentally demonstrated effect in which repeated subclinical stimuli eventually cause a laboratory animal's seizure threshold to decrease, has been postulated to be "LTP 'gone over the top'." J. Mellanby & L. Sundstrom, "Kindling, behaviour, and memory," in T. G. Bolwig et al., ed., *The Clinical Relevance of Kindling*, ch. 7, p. 104 (Chichester, England: John Wiley & Sons 1989).

Accordingly, although electrical stimulation intended to terminate epileptiform activity may have enormous clinical benefits for the patient, it is believed possible that using unduly repetitive or predictable stimulation signal patterns may give a patient's brain the opportunity to learn or acclimate to the patterns, and hence cause the stimulation signal to become less effective over time. Clearly, and consequently, "learning" to dismiss or otherwise process therapeutic electrical stimulation may be detrimental to the efficacy of ongoing therapy. It would be beneficial to be able to avoid this effect when possible, and preferable to be able to maintain a high level of neurostimulation effectiveness over time.

Several known neurostimulators tend to provide irregular stimulation signals as a side effect of attempting to use feedback control mechanisms to adapt to sensed electrographic signals. However, these approaches have not met with consistent success.

U.S. Pat. No. 3,850,161 to Liss describes a feedback-controlled system for counteracting brain electrical energy to control epilepsy. The Liss system is the simplest form of feedback-controlled system: it measures an input signal, and if it exceeds a fixed threshold, an inverted version of the input signal is generated as an output.

In U.S. Pat. No. 5,683,422, Rise describes a system for the treatment of neurodegenerative disorders that measures brain activity, and if brain activity is too high, increases the frequency, pulse width, and/or amplitude of a continuous stimulation signal to attempt to block the sensed activity. The Rise patent does not specifically address the treatment of epileptic seizures, and as described above, continuous stimulation can have certain disadvantages when applied near a seizure focus in the neocortex, regardless of signal modulation.

U.S. Pat. No. 5,522,863 to Spano et al. describes a system and method for applying electrical stimulation to disrupt the chaotic behavior of a neural network, i.e. a population of cells in the brain—epileptiform activity is believed by Spano to be chaotic (short-term deterministic yet long-term unpredictable) in nature. The Spano approach may appear to be effective in modifying certain characteristics in vitro, but its applicability in vivo for treating patients is unclear. And in any event, a device that provides the processing power required to establish the existence of a chaotic system in a human patient and to identify stimulation parameters that might disrupt such a chaotic system in real time would be impractical, especially for use in an implantable system.

In U.S. Pat. No. 6,066,163, John describes an "adaptive brain stimulation" system and method, primarily intended to induce the recovery of patients in a coma state. The John patent describes a system that is directed to the reinforcement of desired electrographic patterns (to achieve a desired brain state) rather than the disruption of undesired patterns, such as those arising out of an electrographic seizure. Moreover, the John system operates not by reinforcing or modifying the signal pattern directly, but by applying specific treatments, checking for progress (comparing electrographic signals to desired patterns), and following up with treatment accordingly.

Accordingly, it is understood that certain forms of neurostimulation may cause certain behaviors of the nervous system to be learned, and hence might reinforce or tend to induce various desirable or undesirable types of electrographic patterns. As epileptic seizures are frequently characterized by repetitive electrographic patterns, a desirable approach to neurostimulation would tend to disrupt, and not to reinforce or cause to be learned, such electrographic patterns.

Even in the systems described above, which are responsive in various ways to sensed electrographic and other signals, stimulation signal timing generally is not directly correlated to features of the measured electrographic signal, even when the stimulation signal is first started. The parameters frequently varied in such schemes are one or more of frequency, amplitude, phase, and pulse duration for a relatively long stimulation waveform - in most cases continuous or semi-continuous stimulation. Accordingly, while the feedback control provides some level of variability to the stimulation signal, the nature of the stimulation signal is still primarily simple and predictable, particularly in light of existing neural activity. The prevailing theory has been that some signal, and nearly any signal, as long as it is applied in a proper location and with sufficient energy, will distract the brain from its undesired synchronous behavior. 100301

However, the prevailing theory might not be universally true, and in any event, stimulation efficacy appears to vary depending at least in part on phase timing and stimulation signal duration. See, e.g., G. K. Motamedi et al., Abstract (AES 1999), "Brief Pulse Stimulation Is More Likely To Terminate Afterdischarges During Their Negative Phase," Epilepsia 1999; 40(Suppl.7): 136.

To reduce the predictability of a stimulation signal, it may be beneficial to cycle through multiple patterns, or templates, for stimulation waveforms. However, as the human brain is particularly complex and adaptable, it may be able to learn and adapt to even relatively complicated therapy rotation schemes.

Accordingly, and for the reasons set forth above, it is desirable to be able to achieve adaptive and less predictable stimulation signal timing, particularly with regard to stimulation signal phase timing, duration, and amplitude in order to correlate with or intentionally desynchronize EEG activity. Such an adaptive stimulation signal would have adaptive, correlated, or otherwise altered characteristics to attempt to avoid learning, conditioning, habituation, and other similar mechanisms, and may have an increased chance of disrupting epileptiform activity.

SUMMARY OF THE INVENTION

In contrast to the known stimulation techniques, the adaptive stimulation system and method of the invention allows a stimulation signal to be adjusted to observed electrographic conditions in real time. This can result in improved results when it is advantageous to stimulate at certain times or with certain stimulation signal parameters to achieve a desired result, when it is desirable to introduce a measure of variability into a stimulation signal to avoid or inhibit undesired learning, conditioning, or habituation, or for both reasons.

A method performed according to the invention for treating a neurological disorder with adaptive stimulation generally begins by detecting an electrographic signal of interest. If the electrographic signal is one for which adaptive stimulation should be applied, the method continues by measuring a characteristic of the electrographic signal, which in a preferred embodiment of the invention is typically a duration or an amplitude of a qualified half wave extracted from the electrographic signal. More than one characteristic can be used. The characteristic is transformed as desired and used to define or modify a stimulation signal, which is then applied preferably at a precise time correlated to a desirable time, which may also be dependent in part on the extracted characteristic.

Accordingly, a system for performing the method described above would generally include an implantable neurostimulator with a detection subsystem, a stimulation subsystem, a central processing unit capable of controlling and coordinating the detection subsystem and the stimulation subsystem, and means of synchronizing stimulation signals to desired events and times.

A system or method according to the present invention is capable of delivering neurostimulation signals that are intentionally altered to provide a measure of variability to stimulation signal timing and other characteristics. This may tend to avoid undesired long-term effects as described above.

Because a neurostimulator according to the invention has multiple detection channels capable of deriving features and characteristics from electrographic signals, no special-purpose circuitry would be necessary to accomplish synchronization, correlation, or alteration according to the invention. In particular, where decorrelation (or pseudo-randomization) is necessary, either a significant quantity of special hardware circuitry or power-intensive software algorithms would typically be necessary to achieve the level of variation desirable to avoid habituation. Accordingly, the approach presented herein is particularly advantageous in that it leverages existing circuitry and algorithms, for example otherwise unused sensing and signal processing channels, to achieve a goal that would otherwise require additional resources.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
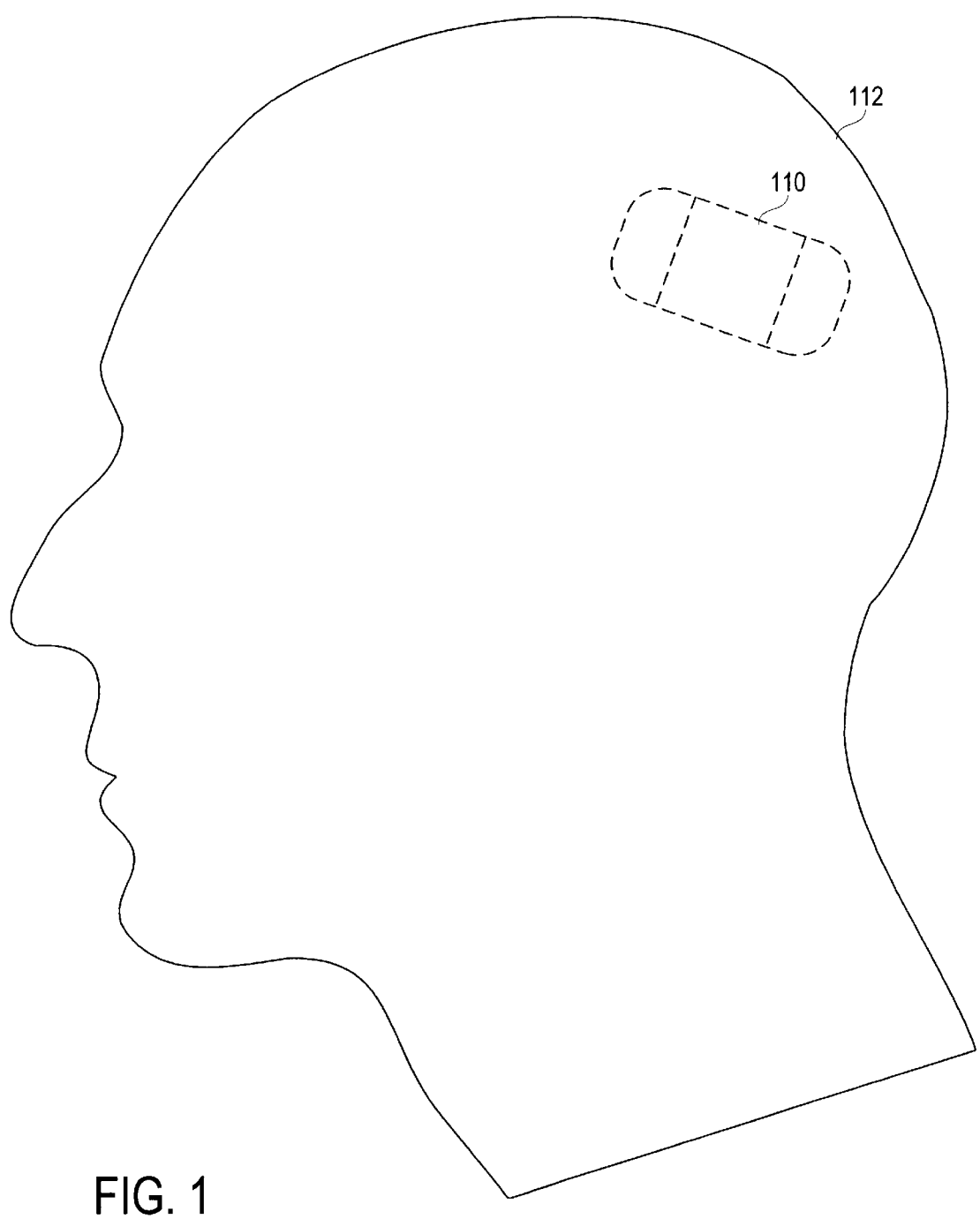
FIG. 1 is a schematic illustration of a patient's head showing the placement of an implantable neurostimulator according to an embodiment of the invention.

FIG. 1 depicts an intracranially implanted device 110 according to the invention, which in one embodiment is a small self-contained responsive neurostimulator. As the term is used herein, a responsive neurostimulator is a device capable of detecting ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator detects and treats epileptiform activity and its symptoms by systems and methods according to the invention.

Figure 2:
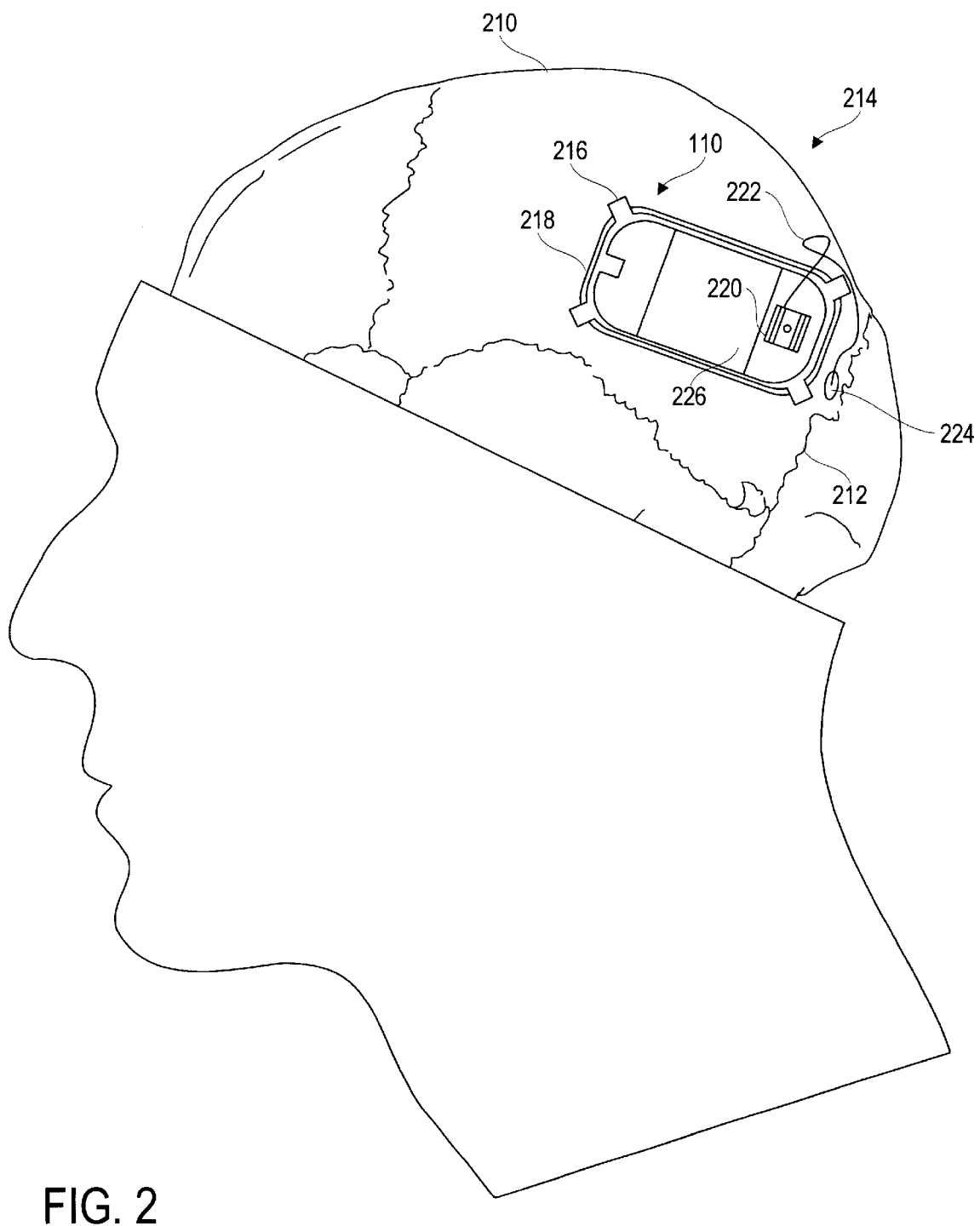
FIG. 2 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 210, in a location anterior to the lambdoidal suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device is implanted under the patient's scalp 112 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating epilepsy by detecting seizure precursors and preventing and/or terminating epileptic seizures.

In an alternative embodiment of the invention, the device 110 does not necessarily need to detect particular neurological events of interest, but can be employed to apply scheduled or continuous stimulation with stimulation characteristics provided and varied according to the invention.

It should be observed that the device 110 is not necessarily just a responsive neurostimulator, but is more broadly considered as an apparatus capable of detecting neurological conditions and events and performing actions in response thereto. The actions performed by such an embodiment of the device 110 need not be exclusively therapeutic, but may involve data recording or transmission, providing warnings to the patient, or any of a number of known alternative actions. Such a device will typically act as a diagnostic device when interfaced with external equipment, as will be discussed in further detail below.

The device 110, as implanted intracranially, is illustrated in greater detail in FIG. 2. The device 110 is affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection to a conductor in the lead 222 coupling an electrode to circuitry within the device 110. The lead connector 220 accomplishes this in a substantially fluid-tight environment with biocompatible materials.

The lead 222, as illustrated, and other leads for use in a system or method according to the invention, is a flexible elongated member having one or more conductors. As shown, the lead 222 is coupled to the device 110 via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode (see FIG. 4) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 to Fischell, et al., which is hereby incorporated by reference as though set forth in full herein, the burr hole 224 is sealed after implantation to prevent further movement of the lead 222; in an embodiment of the invention, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be provided outside of the housing 226 (and potentially integrated with the lead connector 220) to facilitate communication between the device 110 and external devices.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

Figure 3:
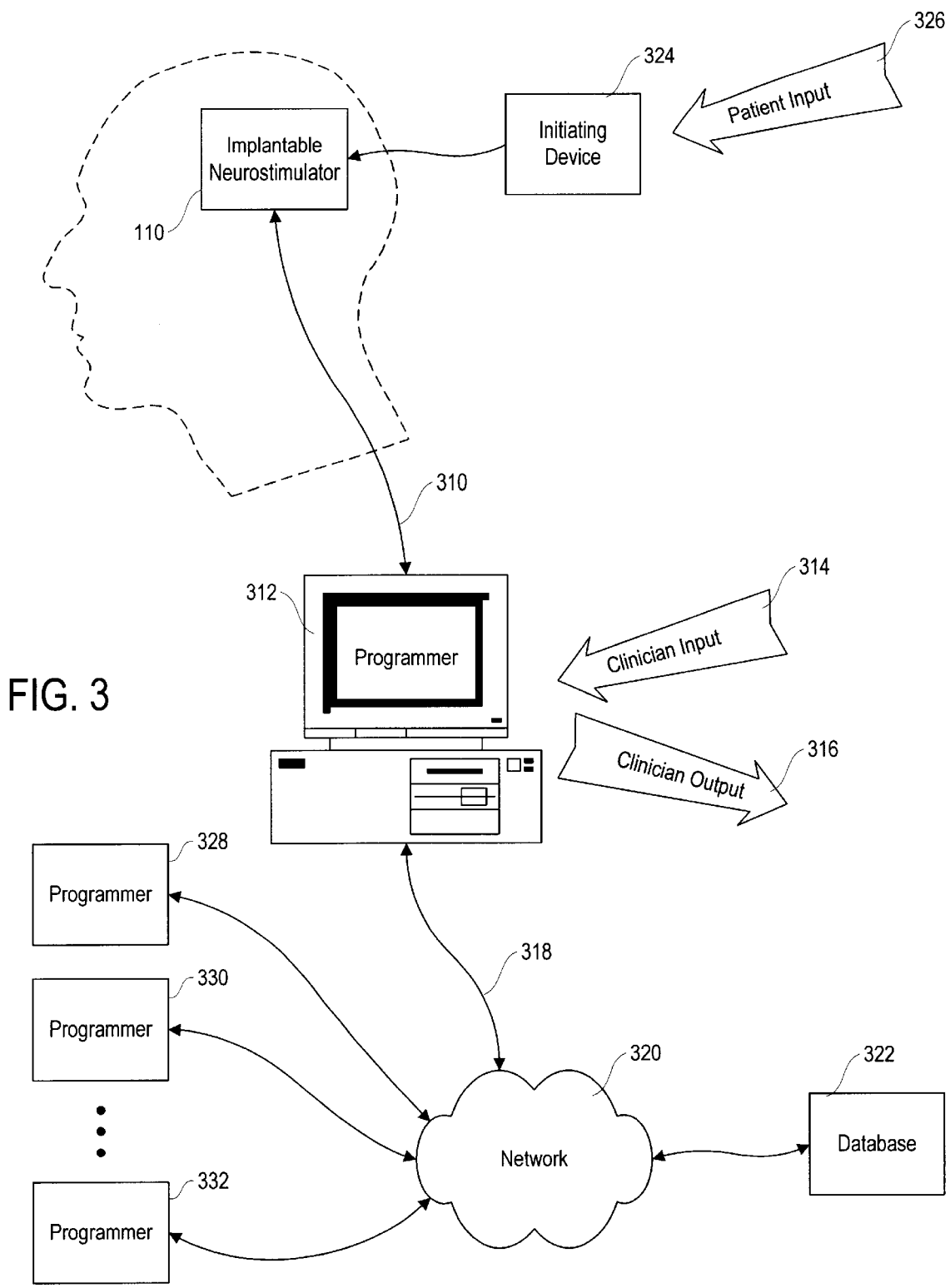
FIG. 3 is a block diagram illustrating a context in which an implantable neurostimulator according to the invention is implanted and operated.

As stated above, and as illustrated in FIG. 3, a neurostimulator according to the invention operates in conjunction with external equipment. The implantable neurostimulator device 110 is mostly autonomous (particularly when performing its usual sensing, detection, and stimulation capabilities), but preferably includes a selectable part-time wireless link 310 to external equipment such as a programmer 312. In the disclosed embodiment of the invention, the wireless link 310 is established by moving a wand (or other apparatus) having communication capabilities and coupled to the programmer 312 into communication range of the implantable neurostimulator device 110. The programmer 312 can then be used to manually control the operation of the device, as well as to transmit information to or receive information from the implantable neurostimulator device 110. Several specific capabilities and operations performed by the programmer 312 in conjunction with the device will be described in further detail below.

The programmer 312 is capable of performing a number of advantageous operations in connection with the invention. In particular, the programmer 312 is able to specify and set variable parameters in the implantable neurostimulator device 110 to adapt the function of the device to meet the patient's needs, upload or receive data (including but not limited to stored EEG waveforms, parameters, or logs of actions taken) from the implantable neurostimulator device 110 to the programmer 312, download or transmit program code and other information from the programmer 312 to the implantable neurostimulator device 110, or command the implantable neurostimulator device 110 to perform specific actions or change modes as desired by a physician operating the programmer 312. To facilitate these functions, the programmer 312 is adapted to receive clinician input 314 and provide clinician output 316; data is transmitted between the programmer 312 and the implantable neurostimulator device 110 over the wireless link 310.

The programmer 312 may be used at a location remote from the implantable neurostimulator device 110 if the wireless link 310 is enabled to transmit data over long distances. For example, the wireless link 310 may be established by a short-distance first link between the implantable neurostimulator device 110 and a transceiver, with the transceiver enabled to relay communications over long distances to a remote programmer 312, either wirelessly (for example, over a wireless computer network) or via a wired communications link (such as a telephonic circuit or a computer network).

The programmer 312 may also be coupled via a communication link 318 to a network 320 such as the Internet. This allows any information uploaded from the implantable neurostimulator device 110, as well as any program code or other information to be downloaded to the implantable neurostimulator device 110, to be stored in a database 322 at one or more data repository locations (which may include various servers and network-connected programmers like the programmer 312). This would allow a patient (and the patient's physician) to have access to important data, including past treatment information and software updates, essentially anywhere in the world that there is a programmer (like the programmer 312) and a network connection. Alternatively, the programmer 312 may be connected to the database 322 over a trans-telephonic link.

In the disclosed embodiment, the implantable neurostimulator device 110 is also adapted to receive communications from an initiating device 324, typically controlled by the patient or a caregiver. Accordingly, patient input 326 from the initiating device 324 is transmitted over a wireless link to the implantable neurostimulator device 110; such patient input 326 may be used to cause the implantable neurostimulator device 110 to switch modes (on to off and vice versa, for example) or perform an action (e.g., store a record of EEG data). Preferably, the initiating device 324 is able to communicate with the implantable neurostimulator device 110 through a communication subsystem 430 (FIG. 4), and possibly in the same manner the programmer 212 does. The link may be unidirectional (as with the magnet and GMR sensor described below), allowing commands to be passed in a single direction from the initiating device 324 to the implantable neurostimulator device 110 but in an alternative embodiment of the invention is bi-directional, allowing status and data to be passed back to the initiating device 324. Accordingly, the initiating device 324 may be a programmable PDA or other hand-held computing device, such as a Palm Pilot® or PocketPC®. However, a simple form of initiating device 324 may take the form of a permanent magnet, if the communication subsystem 430 (FIG. 4) is adapted to identify magnetic fields and interruptions therein as communication signals.

The implantable neurostimulator device 110 (FIG. 1) generally interacts with the programmer 312 (FIG. 3) as described below. Data stored in the memory subsystem 426 can be retrieved by the patient's physician through the wireless communication link 310, which operates through the communication subsystem 430 of the implantable neurostimulator device 110. In connection with the invention, a software operating program run by the programmer 312 allows the physician to read out a history of events detected including EEG information before, during, and after each event, as well as specific information relating to the detection of each:event (such as, in one embodiment, the time-evolving energy spectrum of the patient's EEG). The programmer 312 also allows the physician to specify or alter any programmable parameters of the implantable neurostimulator device 110. The software operating program also includes tools for the analysis and processing of recorded EEG records to assist the physician in developing optimized seizure detection parameters for each specific patient.

In an embodiment of the invention, the programmer 312 is primarily a commercially available PC, laptop computer, or workstation having a CPU, keyboard, mouse and display, and running a standard operating system such as Microsoft Windows®, Linux®, Unix®, or Apple Mac OS®. It is also envisioned that a dedicated programmer apparatus with a custom software package (which may not use a standard operating system) could be developed.

When running the computer workstation software operating program, the programmer 312 can process, store, play back and display on the display the patient's EEG signals, as previously stored by the implantable neurostimulator device 110 of the implantable neurostimulator device.

The computer workstation software operating program also has the capability to simulate the detection of epileptiform activity. Included in the capability to simulate detection of epileptiform activity, the software operating program of the present invention has the capability to allow a clinician to create or modify a patient-specific collection of information comprising, in one embodiment, algorithms and algorithm parameters for epileptiform activity detection. The patient-specific collection of detection algorithms and parameters used for neurological activity detection according to the invention will be referred to herein as a detection template or patient-specific template. The patient-specific template, in conjunction with other information and parameters generally transferred from the programmer to the implanted device (such as stimulation parameters, time schedules, and other patient-specific information), make up a set of operational parameters for the neurostimulator.

Following the development of a patient-specific template on the workstation 312, the patient-specific template would be downloaded through the communications link 310 from the programmer 312 to the implantable neurostimulator device 110.

Preferably, the database 322 is adapted to communicate over the network 320 with multiple programmers, including the programmer 312 and additional programmers 328, 330, and 332. It is contemplated that programmers will be located at various medical facilities and physicians' offices at widely distributed locations. Accordingly, if more than one programmer has been used to upload EEG records from a patient's implantable neurostimulator device 110, the EEG records will be aggregated via the database 322 and available thereafter to any of the programmers connected to the network 320, including the programmer 312.

Figure 4:
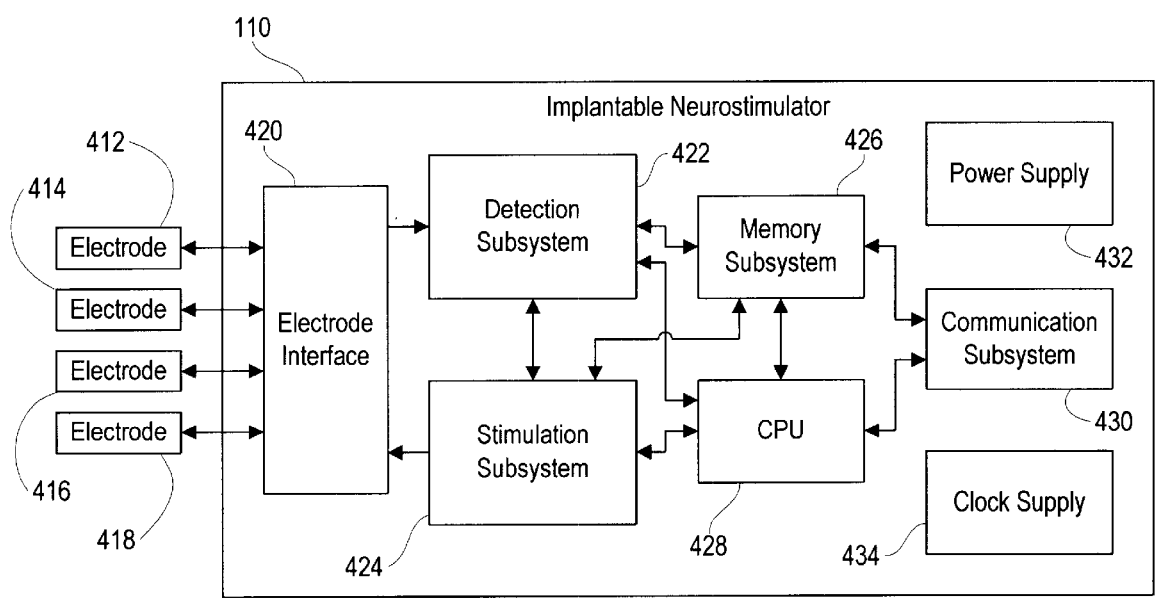
FIG. 4 is a block diagram illustrating the major functional subsystems of an implantable neurostimulator according to the invention.

FIG. 4 depicts a schematic block diagram of a neurostimulator system according to the invention, including an implantable neurostimulator device 110, which in one embodiment is a small self-contained responsive neurostimulator that is intracranially implanted. As the term is used herein, a responsive neurostimulator is a device capable of detecting ictal activity (or other neurological events) and providing electrical stimulation to neural tissue in response to that activity, where the electrical stimulation is specifically intended to terminate the ictal activity, treat a neurological event, prevent an unwanted neurological event from occurring, or lessen the severity or frequency of certain symptoms of a neurological disorder. As disclosed herein, the responsive neurostimulator device 110 detects and responds to ictal activity by systems and methods according to the invention as disclosed herein.

It should be recognized that the embodiment of the device described and illustrated herein is preferably a responsive neurostimulator for detecting and treating epilepsy by detecting seizure precursors and preventing and/or terminating epileptic seizures. However, in an alternative embodiment of the invention, the device is not just a responsive neurostimulator, but is more generally an apparatus capable of detecting neurological conditions and events and performing various actions in response thereto.

FIG. 4 is an overall block diagram of the implantable neurostimulator device 110 used for measurement, detection, and treatment according to the invention. Inside the housing of the neurostimulator device 110 are several subsystems making up the device. The implantable neurostimulator device 110 is capable of being coupled to a plurality of electrodes 412, 414, 416, and 418 (each of which may be individually or together connected to the implantable neurostimulator device 110 via one or more leads) for sensing and stimulation. In the illustrated embodiment, the coupling is accomplished through a lead connector. Although four electrodes are shown in FIG. 4, it should be recognized that any number is possible, and in the embodiment described in detail below, eight electrodes are used. In fact, it is possible to employ an embodiment of the invention that uses a single lead with at least two electrodes, or two leads each with a single electrode (or with a second electrode provided by a conductive exterior portion of the housing in one embodiment), although bipolar sensing between two closely spaced electrodes on a lead is preferred to minimize common mode signals including noise.

The electrodes 412–418 are in contact with the patient's brain or are otherwise advantageously located to receive EEG signals or provide electrical stimulation. Each of the electrodes 412–418 is also electrically coupled to an electrode interface 420. Preferably, the electrode interface is capable of switching each electrode as required between sensing and stimulation functions (or enables both functions simultaneously), and also provides overload protection to the circuitry of the neurostimulator device 110; accordingly the electrode interface is coupled to a detection subsystem 422 and a stimulation subsystem 424. In an alternative embodiment, the electrode interface also may provide any other features, capabilities, or aspects, including but not limited to amplification, isolation, and charge-balancing functions, that are required for a proper interface with neurological tissue and not provided by any other subsystem of the device 110.

The detection subsystem 422 includes and serves primarily as an EEG waveform analyzer; detection is accomplished in conjunction with a central processing unit (CPU) 428. 412–418. The EEG waveform analyzer function is adapted to receive EEG signals from the electrodes through the electrode interface 420, and to process those EEG signals to identify neurological activity indicative of a seizure or a precursor to a seizure. Inventive systems and methods capable of such EEG analysis functionality are described in U.S. patent application Ser. No. 09/896,092 to Pless et al., filed on Jun. 28, 2001 and entitled "SEIZURE SENSING AND DETECTION USING AN IMPLANTABLE DEVICE," which is hereby incorporated by reference as though set forth in full herein. See also U.S. Pat. No.

6,016,449 to Fischell et al., incorporated by reference above, for alternative approaches. The detection subsystem may optionally also contain further sensing and detection capabilities, including but not limited to parameters derived from other physiological conditions (such as electrophysiological parameters, temperature, blood pressure, etc.). In general, prior to analysis, the detection subsystem performs amplification, analog to digital conversion, and multiplexing functions on the signals in the sensing channels received from the electrodes 412–418.

The stimulation subsystem 424 is capable of applying electrical stimulation to neurological tissue through the electrodes 412–418. This can be accomplished in any of a number of different manners. For example, it may be advantageous in some circumstances to provide stimulation in the form of a substantially continuous stream of pulses, or on a scheduled basis. Preferably, therapeutic stimulation is provided in response to abnormal events detected by the EEG analyzer function of the detection subsystem 422. As illustrated in FIG. 4, the stimulation subsystem 424 and the EEG analyzer function of the detection subsystem 422 are in communication; this facilitates the ability of stimulation subsystem 424 to provide responsive stimulation as well as an ability of the detection subsystem 422 to blank the amplifiers while stimulation is being performed to minimize stimulation artifacts. In connection with the current invention, the close connection between the detection subsystem 422 and the stimulation subsystem 424 facilitates time synchronization between a sensed electrographic waveform and a generated stimulation waveform. It is contemplated that the parameters of the stimulation signal (e.g., frequency, duration, waveform) provided by the stimulation subsystem 424 would be specified by other subsystems in the implantable neurostimulator device 110, as will be described in further detail below.

In accordance with the invention, the stimulation subsystem 424 may also provide for other types of stimulation, besides electrical stimulation described above. In particular, in certain circumstances, it may be advantageous to provide audio or tactile signals to the patient, or to provide somatosensory electrical stimulation to the brain or to locations other than the brain.

Also in the implantable neurostimulator device 110 are a memory subsystem 426 and the CPU 428, which can take the form of a microcontroller. The memory subsystem is coupled to the detection subsystem 422 (e.g., for receiving and storing data representative of sensed EEG signals and evoked responses), the stimulation subsystem 424 (e.g., for providing stimulation waveform parameters to the stimulation subsystem), and the CPU 428, which can control the operation of the memory subsystem 426. In addition to the memory subsystem 426, the CPU 428 is also connected to the detection subsystem 422 and the stimulation subsystem 424 for direct control of those subsystems.

Also provided in the implantable neurostimulator device 110, and coupled to the memory subsystem 426 and the CPU 428, is a communication subsystem 430. The communication subsystem 430 enables communication between the device 410 and the outside world, particularly an external programmer and a patient initiating device, both of which are described above with reference to FIG. 3. As set forth above, the disclosed embodiment of the communication subsystem 430 includes a telemetry coil (which may be situated outside of the housing of the implantable neurostimulator device 110) enabling transmission and reception of signals, to or from an external apparatus, via inductive coupling. Alternative embodiments of the communication subsystem 430 could use an antenna for an RF link or an audio transducer for an audio link. Preferably, the communication subsystem 430 also includes a GMR (giant magnetoresistive effect) sensor to enable receiving simple signals (namely the placement and removal of a magnet) from a patient initiating device; this capability can be used to activate or deactivate the device 110, initiate EEG recording, or take other actions enabled by the device 110 and the programming of the CPU 428.

If the stimulation subsystem 424 includes the audio capability set forth above, it may be advantageous for the communication subsystem 430 to cause the audio signal to be generated by the stimulation subsystem 424 upon receipt of an appropriate indication from the patient initiating device (e.g., the magnet used to communicate with the GMR sensor of the communication subsystem 430), thereby confirming to the patient or caregiver that the desired action will be taken. Preferably, the audio capability of the stimulation subsystem 424 can be enabled or disabled on a case-by-case basis, as it might not be beneficial or even suitable in all circumstances.

Rounding out the subsystems in the implantable neurostimulator device 110 are a power supply 432 and a clock supply 434. The power supply 432 supplies the voltages and currents necessary for each of the other subsystems. The clock supply 434 supplies substantially all of the other subsystems with any clock and timing signals necessary for their operation, including a real-time clock signal to coordinate programmed and scheduled actions.

It should be observed that while the memory subsystem 426 is illustrated in FIG. 1 as a separate functional subsystem, the other subsystems may also require various amounts of memory to perform the functions described above and others. Furthermore, while the implantable neurostimulator device 110 is preferably a single physical unit (i.e., a control module) contained within a single implantable physical enclosure, namely the housing described above, other embodiments of the invention might be configured differently. The neurostimulator device 110 may be provided as an external unit not adapted for implantation, or it may comprise a plurality of spatially separate units each performing a subset of the capabilities described above, some or all of which might be external devices not suitable for implantation. Also, it should be noted that the various functions and capabilities of the subsystems described above may be performed by electronic hardware, computer software (or firmware), or a combination thereof. The division of work between the CPU 428 and the other functional subsystems may also vary—the functional distinctions illustrated in FIG. 4 may not reflect the integration of functions in a real-world system or method according to the invention.

In a preferred mode of operation, a system according to the invention continuously receives electrographic input signals through the electrodes 412–418, the electrode interface 420, and the detection subsystem 422. The detection subsystem 422 is capable of detecting neurological events of interest (such as seizures, their onsets, and their precursors), and accordingly is able to signal the CPU 428 when certain analytical conditions are met. The CPU 428 uses programmed criteria to detect and identify neurological events in real time, and moreover is able to schedule non-responsive stimulation events by synchronizing such scheduled events with timing signals generated by the clock supply 434.

Accordingly, the CPU 428 interprets the data from the detection subsystem 422 and the clock supply 434, and when appropriate, signals the stimulation subsystem 424 to apply a therapeutic electrical stimulation signal to the patient's brain through the electrode interface 420 and the electrodes 412–418. As described in further detail below and in connection with the invention described herein, the stimulation subsystem 424 uses electrographic signal criteria and characteristics received from the detection subsystem 422 (generally through the memory subsystem 426 and/or the CPU 428) to generate an adaptive stimulation signal and synchronize it in various ways to the electrographic input signals.

Figure 5:
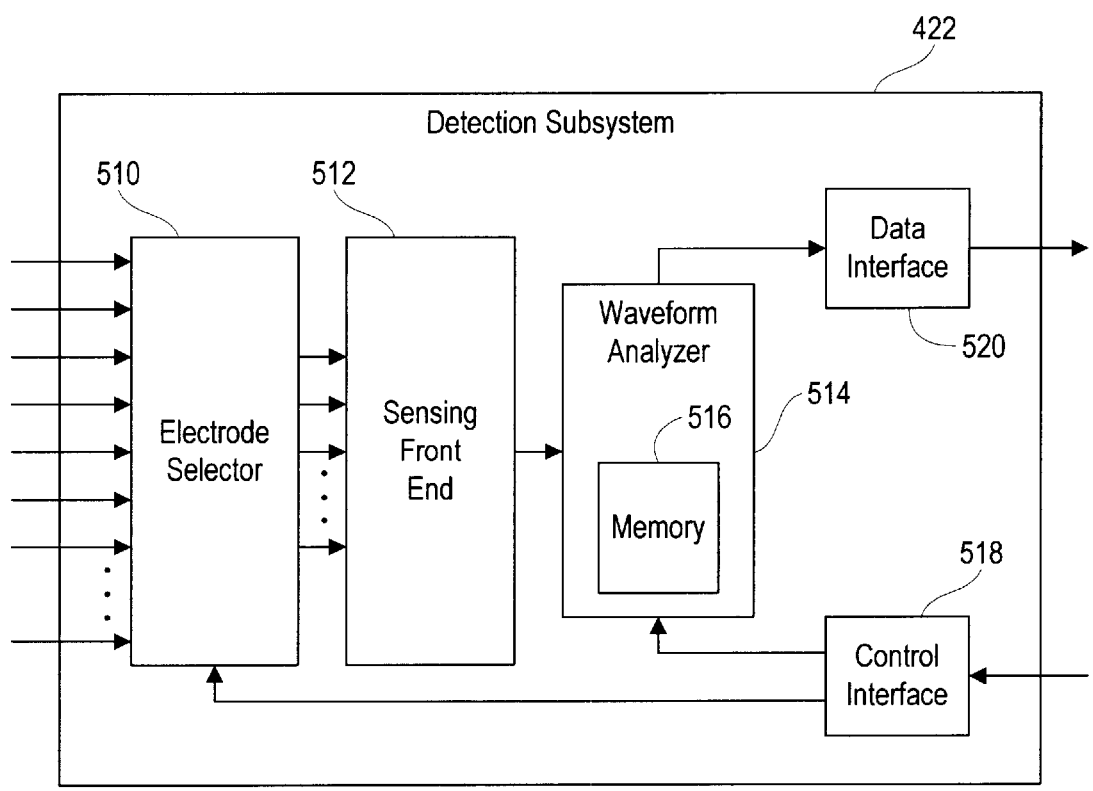
FIG. 5 is a block diagram illustrating the functional components of the detection subsystem of the implantable neurostimulator shown in FIG. 4.

FIG. 5 illustrates details of the detection subsystem 422 (FIG. 4). Inputs from the electrodes 412–418 are on the left, and connections to other subsystems are on the right.

Signals received from the electrodes 412–418 (as routed through the electrode interface 420) are received in an electrode selector 510. The electrode selector 510 allows the device to select which electrodes (of the electrodes 412–418) should be routed to which individual sensing channels of the detection subsystem 422, based on commands received through a control interface 518 from the memory subsystem 426 or the CPU 428 (FIG. 4). Preferably, each sensing channel of the detection subsystem 422 receives a bipolar signal representative of the difference in electrical potential between two selectable electrodes. Accordingly, the electrode selector 510 provides signals corresponding to each pair of selected electrodes (of the electrodes 412–418) to a sensing front end 512, which performs amplification, analog to digital conversion, and multiplexing functions on the signals in the sensing channels. Preferably, any of the electrodes 412-418 can be unused (i.e., not connected to any sensing channel), coupled to a positive or negative input of a single sensing channel, coupled to the positive inputs of multiple sensing channels, or coupled to the negative inputs of multiple sensing channels.

A multiplexed input signal representative of all active sensing channels is then fed from the sensing front end 512 to a:waveform analyzer 514. The waveform analyzer 514 is preferably a special-purpose digital signal processor (DSP) adapted for use with the invention, or in an alternative embodiment, may comprise a programmable general-purpose DSP. In the disclosed embodiment, the waveform analyzer has its own scratchpad memory area 516 used for local storage of data and program variables when the signal processing is being performed. In either case, the signal processor performs suitable measurement and detection methods described generally above and in greater detail below.

As described in U.S. patent application Ser. No. 09/896, 092, referenced above, a responsive neurostimulator according to the invention is capable of using three different kinds of analysis tools in various combinations, namely a half wave analysis tool, a line length analysis tool, and an area analysis tool. There are preferably multiple instances of each analysis tool, each of which can be set up with different detection parameters and coupled to a different input sensing channel if desired.

The half wave analysis tool measures characteristics of an EEG signal related to the signal's dominant frequency content. In general terms, a half wave is an interval between a local waveform minimum and a local waveform maximum; each time a signal "changes directions" (from increasing to decreasing, or vice versa), subject to limitations that will be set forth in further detail below, a new half wave is identified.

The identification of half waves having specific amplitude and duration criteria allows some frequency-driven characteristics of the EEG signal to be considered and analyzed without the need for computationally intensive transformations of normally time-domain EEG signals into the frequency domain. Specifically, the half wave feature extraction capability of the invention identifies those half waves in the input signal having a duration that exceeds a minimum duration criterion and an amplitude that exceeds a minimum amplitude criterion. The number of half waves in a time window meeting those criteria is somewhat representative of the amount of energy in a waveform at a frequency below the frequency corresponding to the minimum duration criterion. And the number of half waves in a time window is constrained somewhat by the duration of each half wave (i.e., if the half waves in a time window have particularly long durations, relatively fewer of them will fit into the time window), that number is highest when a dominant waveform frequency most closely matches the frequency corresponding to the minimum duration criterion.

Accordingly, the number of qualified half waves (i.e., half waves meeting both the duration criterion and the amplitude criterion) within a limited time period is a quantity of interest, as it may be representative of neurological events manifested in the specified frequency range corresponding to the half wave criteria.

The line length analysis tool is a simplification of waveform fractal dimension, allowing a consideration of how much variation an EEG signal undergoes. Accordingly, the line length analysis tool according to the invention enables the calculation of a "line length" for an EEG signal within a time window. Specifically, the line length of a digital signal represents an accumulation of the sample-to-sample amplitude variation in the EEG signal within a time window. Stated another way, the line length is representative of the variability of the input signal. A constant input signal will have a line length approaching zero (representative of substantially no variation in the signal amplitude), while an input signal that oscillates between extrema from sample to sample will approach the maximum line length. It should be noted that while "line length" has a mathematical-world analogue in measuring the vector distance traveled in a graph of the input signal, the concept of line length as treated herein disregards the horizontal (X) axis in such a situation. The horizontal axis herein is representative of time, which is not combinable in any meaningful way in accordance with the invention with information relating to the vertical (Y) axis, generally representative of amplitude, and which in any event would contribute nothing of interest.

The area analysis tool is a simplification of waveform energy. Accordingly, the area analysis tool according to the invention enables the calculation of the area under the EEG waveform curve within a time window. Specifically, the area function is calculated as an aggregation of the EEG's signal total deviation from zero over the time window, whether positive or negative. The mathematical-world analogue for the area function is the mathematical integral of the absolute value of the EEG function (as both positive and negative signals contribute to positive energy). Once again, the horizontal axis (time) makes no contribution to the area under the curve as treated herein. Accordingly, an input signal that remains around zero will have a small area, while an input signal that remains around the most-positive or most-negative values (or oscillates between those values) will have a high area.

In connection with the present invention, the waveform analyzer 514 is adapted to derive parameters from an input signal not only for detection purposes, but also to achieve the desired stimulation timing according to the invention. It is useful for a waveform analyzer 514 according to the invention to have multiple mappable channels, allowing at least a single channel to be configured specifically to derive signal timing for adaptive stimulation signal synchronization, and other channels to be used for event detection. See U.S. patent application Ser. No. 09/896,092, referenced above, for details on a multi-channel detection subsystem programmable as described herein.

The half wave analysis tool is particularly useful for providing adaptive stimulation parameters according to the invention, as qualified half waves derived as set forth above are discrete and identifiable features of an electrographic waveform that have well-defined amplitudes, durations, and start and end times that are advantageously mappable to stimulation signal characteristics.

There are multiple instances and channels of half wave analysis tools, as described above, and the multiple instances can analyze separate input channels with different signal processing and detection parameters. It should be noted that this capability is particularly advantageous in connection with the present invention, as certain signal processing and half wave detection parameters may be used for neurological event detection and others used for synchronization and adaptive stimulation as described herein. In particular, certain qualified half waves, namely those signal half waves meeting minimum amplitude and minimum duration criteria useful for event detection, may not be best suited for stimulation timing. Therefore, it is generally preferable to dedicate one instance of the half wave analysis tool to deriving qualified half waves specifically for use as synchronization points for adaptive stimulation, as will be described in further detail below. This half wave analysis tool can receive either the same signal that is used for detection or a different signal, depending on how the neurostimulator device 110 is programmed and configured.

Any results from the detection methods described above, as well as any digitized signals intended for storage and subsequent transmission to external equipment, are passed to various other subsystems of the control module 410, including the memory subsystem 426 and the CPU 428 (FIG. 4) through a data interface 520. Similarly, the control interface 518 allows the waveform analyzer 514 and the electrode selector 510 to be in communication with the CPU 428.

Figure 6:
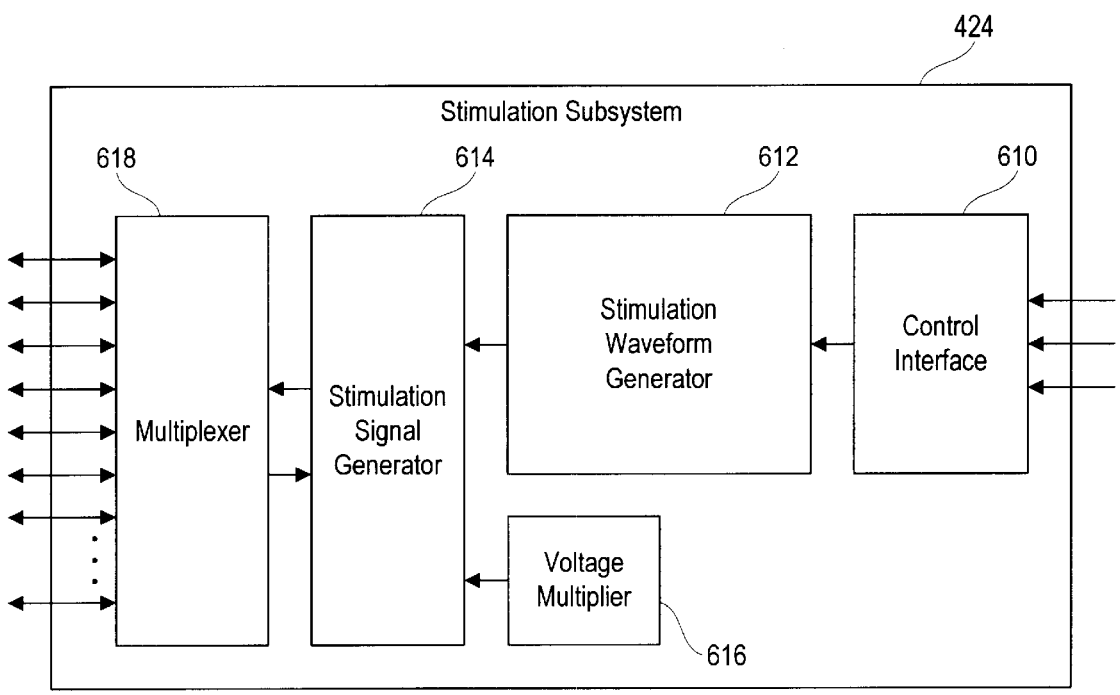
FIG. 6 is a block diagram illustrating the functional components of the stimulation subsystem of the implantable neurostimulator shown in FIG. 4.

Again, the functional distinctions illustrated in FIG. 5, which are presented as separate functions for clarity and understandability herein, might not be meaningful distinctions in an implementation of the invention The various functions and capabilities of the stimulation subsystem 424 are illustrated in greater detail in FIG. 6. Consistent with FIG. 4, inputs to the stimulation subsystem 424 are shown on the right, and outputs are on the left.

Referring initially to the input side of FIG. 6, the stimulation subsystem 424 includes a control interface 610, which receives commands, data, and other information from the CPU 432, the memory subsystem 430, and the detection subsystem 422. The control interface 610 uses the received commands, data, and other information to control a stimulation waveform generator 612. The stimulation waveform generator 612 is adapted to provide the waveforms of electrical stimulation signals appropriate for application to neurological tissue to terminate a present or predicted undesired neurological event, especially an epileptic seizure (or its precursor). Various specific capabilities of the stimulation waveform generator 612 will be described in detail below. As set forth above and described below, the stimulation waveform generator 612 is typically activated in response to conditions detected by the detection subsystem 422 or to a programmed time schedule, but may also provide on-demand stimulation when commanded or substantially continuous stimulation. The various forms of stimulation described above may be programmed or commanded by a clinician using the programmer 312 (FIG. 3).

The stimulation waveform generator 612 is coupled to a stimulation signal generator 614. The stimulation signal generator 614 receives commands and data from the stimulation waveform generator 612, and generates electrical stimulation signals having the desired characteristics that are properly time-scheduled and synchronized according to the invention. The stimulation signal generator 614 receives power from a controllable voltage multiplier 616 to facilitate the application of a proper current (or voltage) to the desired neurological tissue. Preferably, in conjunction with the voltage multiplier 616, the stimulation signal generator 614 acts as a current source and sink that is capable of delivering a precisely controlled current across at least a pair of the electrodes 412–418 (FIG. 4). The voltage multiplier 616 is capable of creating relatively high voltages from a battery power source, which typically has a relatively low voltage; circuits to accomplish this function are well known in the art of electronics design.

The stimulation signal generator 614 applies the electrical current to the electrodes 412–418 (FIG. 4) through a multiplexer 618, which in a preferred embodiment of the invention is capable of selecting a set of electrodes through which the electrical current is to be applied. The multiplexer 618 couples at least one delivery electrode to the current source of the stimulation signal generator 614 and at least one return electrode to the current sink of the stimulation signal generator 614. Accordingly, the multiplexer 618 has a plurality of outputs, which in the disclosed embodiment are coupled to the electrode interface 420 (FIG. 4).

The stimulation waveform generator 612 is invoked by the CPU 428 via the control interface 610 when it is time to perform the stimulation required by the invention. In general, when an event is detected by the neurostimulator device 110, or when a selected and pre-programmed time has been reached, the CPU 428 is activated and caused to schedule an interrupt to occur when the scheduled stimulation is programmed to start. The CPU 428 preferably programs the interrupt to occur a short time before scheduled stimulation to allow for any pre-stimulation "warm up" or pre-processing to be accomplished by the stimulation subsystem 424; a stimulation waveform generated according to the invention (as described below) can be given a built-in delay to accommodate for such a warm up period. The scheduling process will be discussed in further detail below with reference to FIGS. 8–11.

The waveform analyzer 514 of the detection subsystem 422 is also able to generate interrupts for the CPU 428, and certain scheduling tasks can make use of this capability.

It should be recognized that while various functional blocks are illustrated in FIG. 6, not all of them might be present in an operative embodiment of the invention. Furthermore, as with the overall block diagram of FIG. 4, the functional distinctions illustrated in FIG. 6, which are presented as separate functions for clarity and understandability herein, might not be meaningful distinctions in an implementation of the invention.

Figure 7:
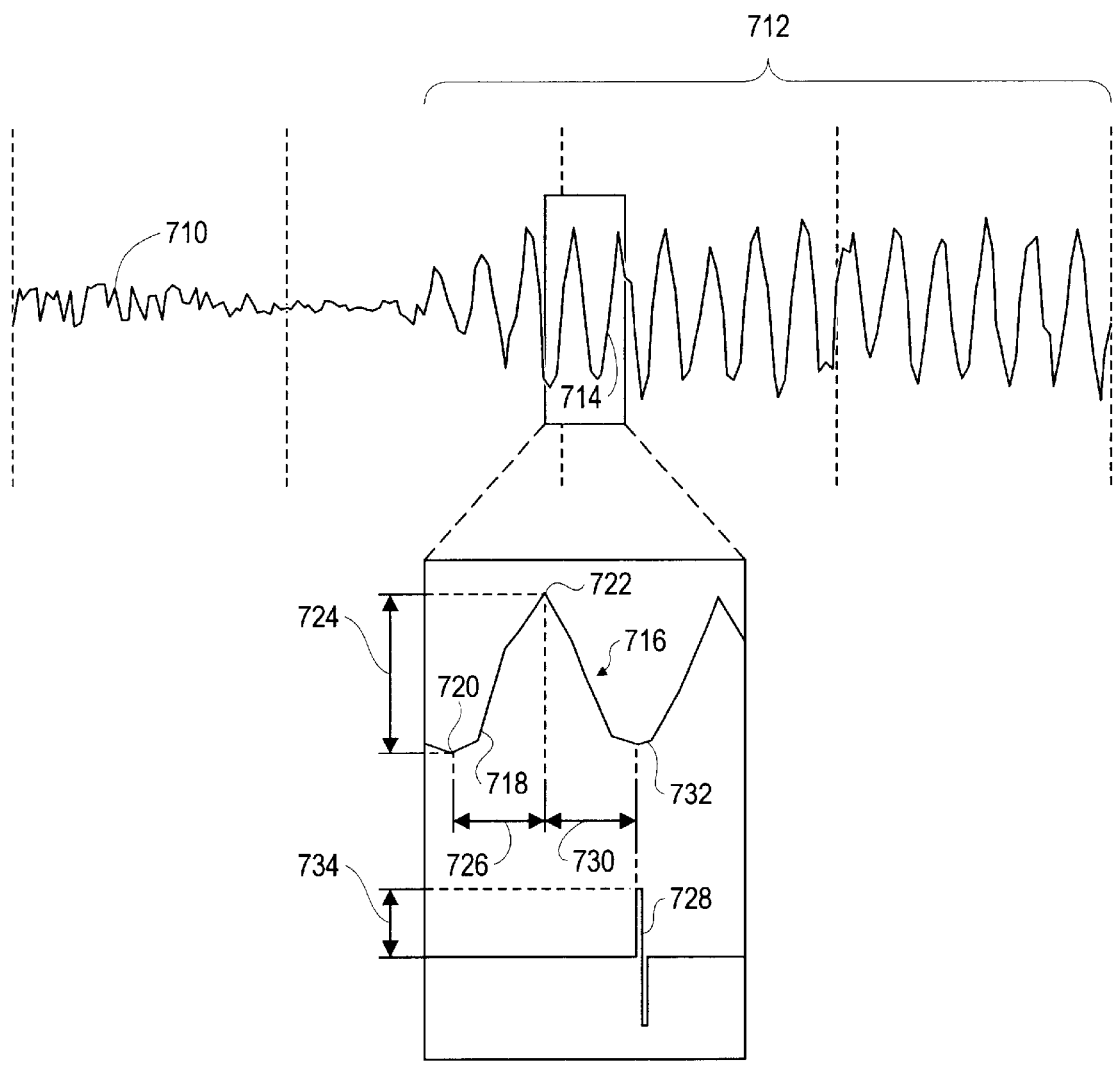
FIG. 7 is an exemplary electrographic waveform depicting the onset and first portion of a seizure, with a portion of the waveform magnified and compared to a stimulus waveform delivered according to a first embodiment of the invention.

Referring now to FIG. 7, an exemplary electrographic waveform 710 is illustrated in conjunction with a stimulation pulse timed according to an embodiment of the invention. The electrographic waveform 710, which is of the general type that would be received and processed by the implantable neurostimulator device 110 of the invention (via the electrodes 412–418, passed through the electrode interface 420 to the detection subsystem 422), has a seizure portion 712 that clearly visually represents rhythmic epileptiform activity. The specific characteristics of the waveform 710 are exemplary only and for purposes of illustration; they are not necessarily intended to reflect a possible real-world scenario. It should be noted in particular that although the seizure portion 712 of the electrographic waveform 710 is clearly apparent in FIG. 7, that would not necessarily be the case in an actual implementation of a system according to the invention.

A small segment 714 of the seizure portion 712 is magnified and shown as a magnified segment 716. The magnified segment 716 will be used to illustrate the derivation of waveform characteristics of interest according to the invention. As illustrated, an increasing half wave 718 represents a substantially monotonic (exclusive of a small hysteresis allowance) increasing portion of the magnified segment 716 between a local minimum 720 and a local maximum 722 of the waveform 710. The amplitude difference (on the Y axis) between the local minimum 720 and the local maximum 722 is the amplitude 724 of the half wave, and the time difference (on the X axis) between the local minimum 720 and the local maximum 722 is the duration 726 of the half wave. If the amplitude 724 and duration 726 exceed respective thresholds, then the observed half wave is considered a "qualified half wave," and is generally regarded as representative of the dominant frequency and amplitude of the electrographic waveform. If the observed half wave does not meet the thresholds, it is disregarded. For details on half wave measurement, see, e.g., U.S. patent application No. 09/896,092, referenced above. It should be noted that even if a qualified half wave meets minimum amplitude and duration thresholds, it is not necessarily truly representative of the underlying signal's frequency or wavelength; it is only a single measurement from what is likely a complex waveform.

As will be described in further detail below, once an event detection has been made, the amplitude 724 and duration 726 are used in various ways by a system according to an embodiment of the invention to synchronize or desynchronize a stimulation signal to the waveform 710.

As illustrated in FIG. 7, in one embodiment of the invention, a biphasic stimulation pulse 728 is applied after a time delay 730 equal in length to the duration 726, thereby approximately synchronizing the pulse 728 to an expected trough 732 in the waveform 710. It should be recognized, of course, that the duration of a qualified half wave is not necessarily accurately representative of the wavelength of the electrographic waveform 710 in the seizure portion 712 (because of variations in the waveform 710 and in the individual half waves making up the waveform 710), so in practice it is unlikely that the pulse 728 will be accurately synchronized to the trough 732. However, after a delay of only one additional half wave duration 726, it is expected that the pulse 728 and the trough 732 may be relatively close.

After a delay of multiple half wave durations, or after significant processing latency, synchronization is less likely and decorrelation will generally be the primary outcome. Accordingly, if the time delay 730 is set to be a multiple (or some other mathematical transform) of the duration 726, or if there is a significant amount of latency between measurement of half wave amplitude 724 and duration 726 and when a stimulation pulse 728 is applied, the delay 730 will generally desynchronize stimulation from the waveform 710 as a result of accumulated error and changes in the characteristics of the waveform 710. As described above, in an embodiment of the invention, this may desirably serve as a variable factor in stimulation to decrease the likelihood of undesired learning of stimulation characteristics.

In an alternative embodiment of the invention, if desired, a pulse amplitude 734 can be correlated to the half wave amplitude 724 in a similar manner, or both amplitude 724 and duration 726 can be mapped onto a stimulation pulse.

It should be noted that while a single biphasic pulse is illustrated in FIG. 7, that pulse is not necessarily to scale and is intended only to illustrate an exemplary timing relationship between the magnified segment 716 and the start of the pulse 728. The amplitude of the pulse 728 may not have the illustrated relationship to the waveform 710. And in an alternative embodiment, the pulse 728 may have a waveform other than a short biphasic pulse, or may be the first portion of a regular or irregular burst of pulses or other signals.

Figure 8:
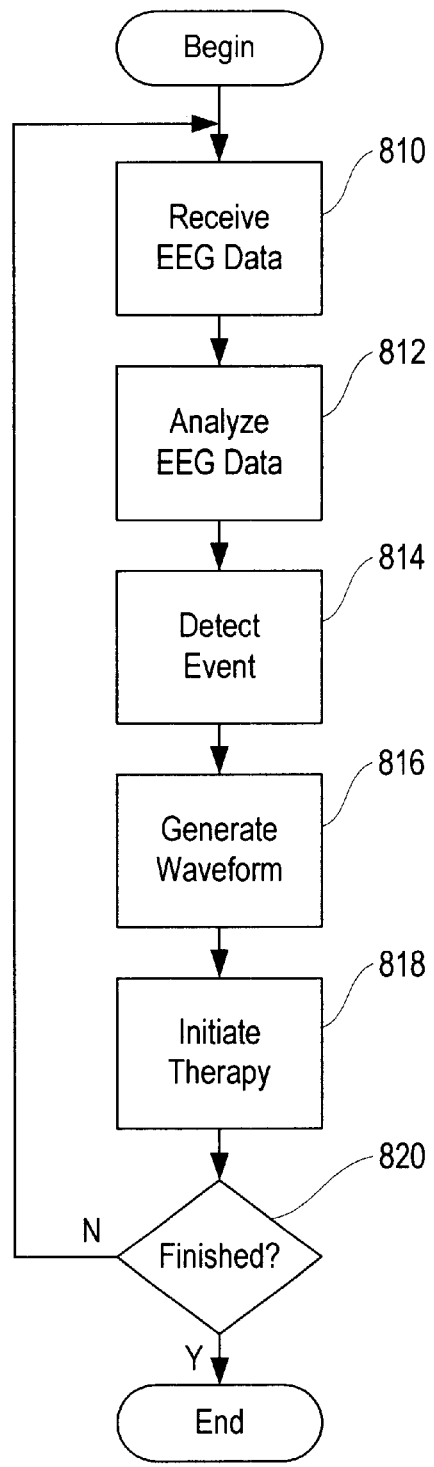
FIG. 8 is a flow chart illustrating the steps performed in applying adaptive electrical stimulation therapy based on electrographic signal characteristics according to an embodiment of the invention.

FIG. 8 depicts a flow chart illustrating the method by which a neurostimulation system (such as the implantable neurostimulator device 110, FIG. 1) provides adaptive therapy according to an embodiment of the invention. Initially, the system receives EEG data or other electrographic signals (step 810)—this is generally performed on a continuous basis, alongside and in parallel with any other detection and other operations performed by the neurostimulator device 110. Also preferably concurrently, the EEG data is analyzed (step 812), and in one embodiment, qualified half waves are identified by the detection subsystem 422 as described above and their characteristics are stored in a first-in-first-out (FIFO) queue or similar data buffer for later retrieval.

Figure 9:
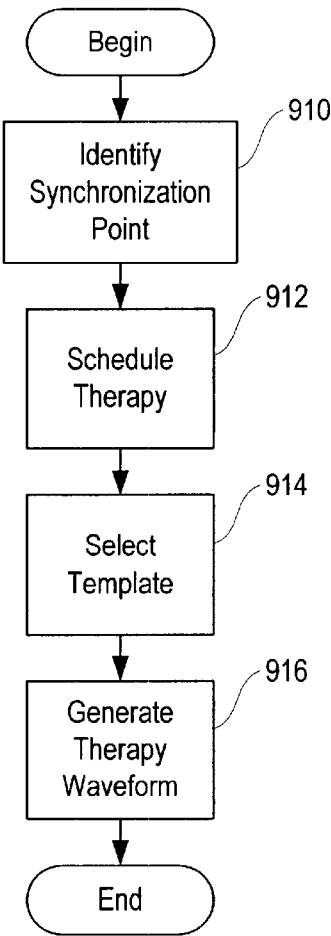
FIG. 9 is a flow chart illustrating the steps performed in generating a treatment template for adaptive electrical stimulation therapy according to the first embodiment of the invention.
Figure 11:
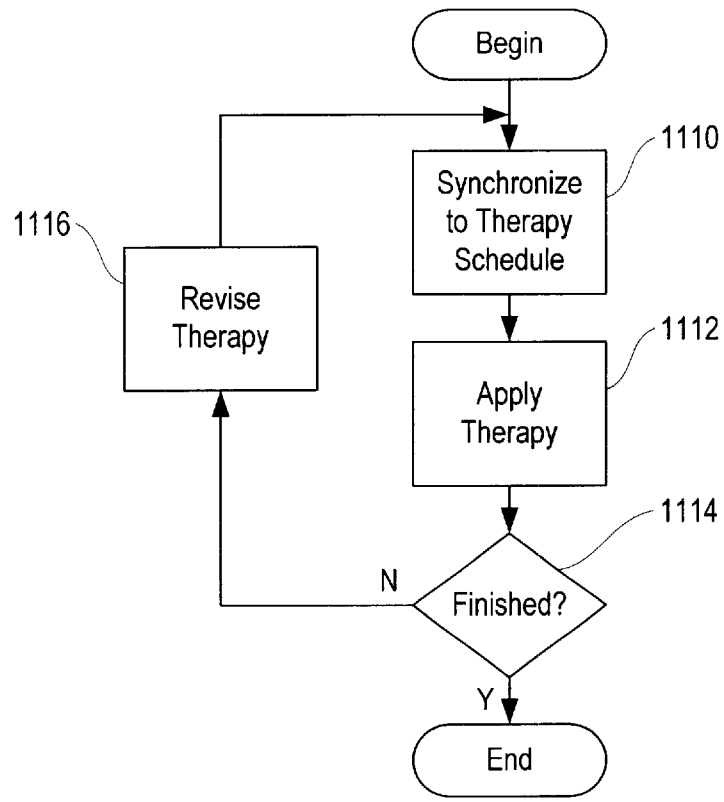
FIG. 11 is a flow chart illustrating the steps performed in delivering adaptive electrical stimulation therapy according to the first embodiment of the invention.

A neurological event is then detected (step 814), or some other time-related event occurs (such as receipt of a time scheduling interrupt from the CPU 428). Following the event, a treatment waveform, including stimulation time and signal details, is generated (step 816). The treatment waveform generation process is illustrated in FIG. 9 and described below, and generally involves extracting information from a measured electrographic signal via the detection subsystem 422 and generating a waveform representative of an adaptive stimulation signal based on the extracted information. Application of the generated stimulation therapy is then initiated (step 818) at the appropriate time. The process used to initiate therapy is illustrated in FIG. 11 and described below. Preferably, stimulation is applied in parallel with other operations performed by the implantable neurostimulator device 110, so even while stimulation is ongoing, if the neurostimulator device 110 is not finished applying adaptive stimulation therapy (step 820), the process of FIG. 8 can repeat as necessary.

The process of generating a treatment waveform is illustrated in detail in FIG. 9. Initially, a time synchronization point is identified (step 910). As described above, this is generally accomplished by identifying a specific half wave of interest and establishing the end point of that half wave as a reference point for the synchronization point (though other reference points are also possible, based on processing windows, real time, and other timers accessible by a neurostimulator according to the invention). The process of identifying a time synchronization point is illustrated in detail in FIG. 10 and will be described below. The synchronization point is used by the CPU 428 to schedule therapy application (step 912) by setting up a specific timer interrupt according to the clock supply 434 (FIG. 4). A therapy pattern template (for example, a single pulse, a burst of pulses, or some other waveform) is then selected and associated with the schedule (step 914). In the disclosed embodiment of the invention, one or more possible therapy templates are stored in the memory subsystem 426 and are made accessible to the CPU 428 and the stimulation subsystem 424. It should be noted, however, that if selection of a desired template from a plurality of templates is not an aspect of the particular adaptive stimulation employed in an embodiment of the invention, then selection of a template (step 914) can be performed before the synchronization point is identified (step 910) or the therapy application is scheduled (step 912); template selection in such a circumstance does not need to be in a time-critical processing path.

It should be noted that the synchronization point may be obtained from substantially any input channel of a neurostimulator according to the invention. To synchronize stimulation to a neurologically significant input signal, it is generally most effective to use the same input channel for event detection, synchronization, and stimulation. However, to achieve intentional desynchronization or other alteration according to the invention, it may be preferable to derive the synchronization information from a separate channel, which is more likely to have characteristics that are substantially independent from and unaffected by a channel used for detection, stimulation, or transformation of a therapy template. The synchronization point may further be obtained or derived from some other source of information less directly associated with or even unrelated to input channels, such as the clock supply 434 (FIG. 4); this would also tend to achieve variability with respect to neurological activity.

In an alternative embodiment of the invention, three separate channels may be used for event detection, synchronization and extraction of parameters for therapy template transformation, and stimulation. And in a further embodiment, four separate channels may be used for event detection, synchronization, extraction of parameters for therapy template transformation, and stimulation. It is particularly advantageous to be able to provide as much configuration flexibility as possible for varying patient clinical needs.

Although it is generally considered advantageous to be able to modify a single therapy pattern template via characteristics of a measured electrographic signal (as in the electrographic waveform 710), it should be observed that in an embodiment of the invention, one aspect of the waveform generation process might be to select a desired template from a collection of multiple templates based on signal characteristic.

A stimulation waveform is then generated (step 916) according to the selected therapy template and any desired parameters identified in the synchronization point. Data representative of the actual stimulation waveform, as generated and based upon the therapy template and the parameters of the synchronization point, are stored in the memory subsystem 426 for access by the stimulation subsystem 424.

To generate the stimulation waveform according to the selected therapy template and any desirable characteristics extracted from the synchronization point, as indicated in step 916, a system or method according to the invention is capable of transforming the therapy template in various ways. For example, as described above, the time of the synchronization point is generally used to schedule the delivery of the stimulation waveform. In an alternative embodiment of the invention, the waveform is generated according to not only time synchronization information, but also according to other aspects of the synchronization point.

For example, if the synchronization point represents a qualified half wave, the time, amplitude, and duration of the qualified half wave and the interval between qualified half waves can be used to select or alter the polarity or amplitude of one or more pulses in the stimulation waveform or the therapy template as a whole; to govern the frequency, inter-pulse interval, or pulse width of the stimulation waveform if the desired therapy template is a burst of pulses or some other repeating pattern; or to choose one of a set of possible therapy templates by mapping the desired characteristic of the synchronization point onto a look-up table of therapy templates.

It should be noted that for purposes of increased variation according to the invention, it is not necessary to map electrographic signal characteristics to their analogous counterparts in the stimulation waveform. For example, it may be appropriate in certain circumstances to cause the amplitude of a qualified half wave to modify the duration of a stimulation waveform, or for a qualified half wave duration to specify the maximum amplitude in a burst of pulses. Preferably, a neurostimulator according to the invention is programmable to accomplish whatever form or combination of adaptive stimulation characteristics is found to be advantageous in a particular clinical setting.

Figure 10:
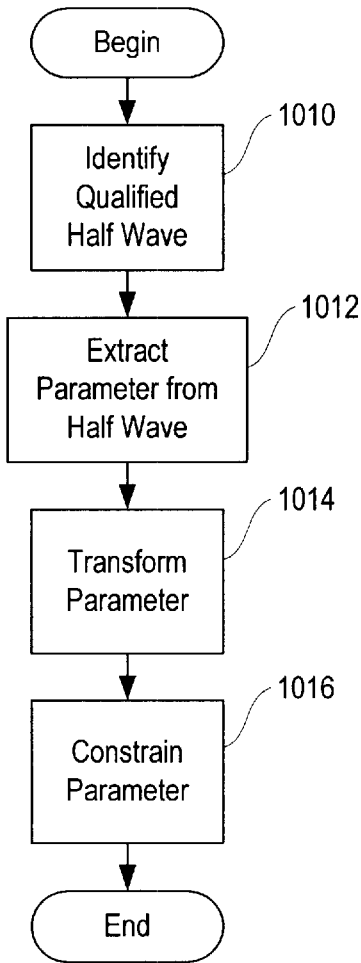
FIG. 10 is a flow chart illustrating the steps performed in synchronizing a treatment template for adaptive electrical stimulation therapy according to the first embodiment of the invention to a feature of an electrographic signal received from the patient.

As generally described above, the method used to identify a synchronization point in an embodiment of the invention is shown in detail in FIG. 10. As stated above, qualified half waves are continuously placed in a FIFO queue. When a neurological event is detected or the application of adaptive stimulation is deemed desirable, the most recent qualified half wave in the queue is identified (step 1010), and the desired parameter (namely one or more of the duration, amplitude, or possibly others) is extracted (step 1012). The extracted parameter is then transformed as desired (step 1014), either linearly or nonlinearly. For example, the extracted parameter can be transformed linearly in one advantageous embodiment by multiplying it by a fixed or variable scale factor and adding a fixed or variable offset. In an embodiment of the invention, stimulation can be approximately synchronized to the analyzed EEG waveform by scheduling a stimulation pulse to occur after the end of the most recent qualified half wave by a fixed delay between approximately 0 and 250 milliseconds, a percentage of the delay between 0 and 100% of the measured interval between waves, or a combination of fixed and interval-dependent delays. In the disclosed-embodiment of the invention, the measured interval between waves is preferably calculated as the time delay between successive qualified half waves, as stored in the FIFO queue.

If desired, the parameters extracted from recent qualified half waves, as transformed, are constrained by minimum and maximum values (step 1016). Preferably, the adaptive interval-based delay described above is constrained by programmable minimum and maximum values between about 0 and 250 milliseconds.

For a burst of pulses, not only can the timing of the first pulse be governed by a fixed or interval-dependent delay, but the inter-pulse interval can also be controlled in a similar manner. For example, either the duration or the interval of qualified half waves in the FIFO queue can be used to control the inter-pulse interval, and qualified half wave amplitudes can be used to modify the amplitudes of subsequent pulses, or of the burst as a whole. Generally, controlling the parameters of each pulse of a burst separately would be advantageously accomplished by scheduling each pulse in the burst as a separate stimulation event, and causing the methods of the invention to extract information from the electrographic signal and generate an adaptive pulse for each separately scheduled stimulation event.

Many possible uses of the parameters described above are possible. To provide decorrelation, rather than synchronization, as discussed above, it is possible to map qualified half wave duration or interval to stimulation amplitude, or qualified half wave amplitude to stimulation timing or frequency, for example. In other detection schemes, such as those reliant on waveform line length or area, as described above, parameters related to those measurements can also be used to provide a measure of variability to a stimulation signal.

Similar waveform shaping and timing considerations can be applied to other stimulation waveforms, as well. To provide but one example, the frequency of sinusoidal stimulation may be derived from the half wave interval. Other possibilities consistent with the invention should be apparent.

Therapy is initiated and applied at the appropriate time according to the method illustrated in the flow chart of FIG. 11. As shown in FIG. 10, delivery of stimulation is scheduled by the CPU 428 (FIG. 4) and tied to a timer interrupt. When the timer interrupt is received, synchronization to the therapy schedule has been accomplished (step 1110), and the CPU 428 commands the stimulation subsystem 424 (and in particular the stimulation waveform generator 612 and the stimulation signal generator 614, FIG. 6) to deliver the appropriate stimulation signal, thereby applying stimulation therapy to the patient (step 1112). The nature of the desired stimulation waveform, if it is simple, can be expressed in the command from the CPU 428, or alternatively, a representation of the desired stimulation waveform, if stored in the memory subsystem 426, can be caused by the CPU 428 to be streamed to the stimulation subsystem 424. If there are additional scheduled pulses or waveforms to be applied, therapy application is not complete (step 1114), the therapy plan is optionally revised (step 1116), and the synchronization and application steps (1110–1112) are repeated as necessary.

In a maximally flexible embodiment of the invention, after each pulse or waveform segment is delivered, the remaining portion of a therapy plan can be revised, resynchronized, retransformed, or otherwise altered in a manner similar to that set forth in FIG. 9 and described above. In particular, it would be advantageous, if desired, to be able to identify a new synchronization point (step 910) and reschedule therapy (step 912), thereby allowing each pulse or segment of a stimulation waveform to be individually synchronized, correlated, or otherwise altered with respect to a sensed signal. It may also be advantageous in some circumstances to be able to select a new therapy pattern template (step 914) or regenerate the therapy waveform (step 916), or both, according to newly measured characteristics of an input electrographic waveform on any desired channel of the neurostimulator device 110.

In an embodiment of the invention, to achieve variation in stimulation timing, it may be possible to synchronize the delivery of stimulation to events other than a synchronization point (step 910) that corresponds to some characteristic or feature of an electrographic signal. For example, it may be desirable to synchronize to timer interrupts generated by the clock supply 434 of the neurostimulator device 110, or to any other event or time ascertainable by a subsystem of the neurostimulator device 110.

As described above, the therapy application process of FIG. 11 preferably is able to operate in parallel with other operations performed by the implantable neurostimulator device 110 (FIG. 1).

Figure 12:
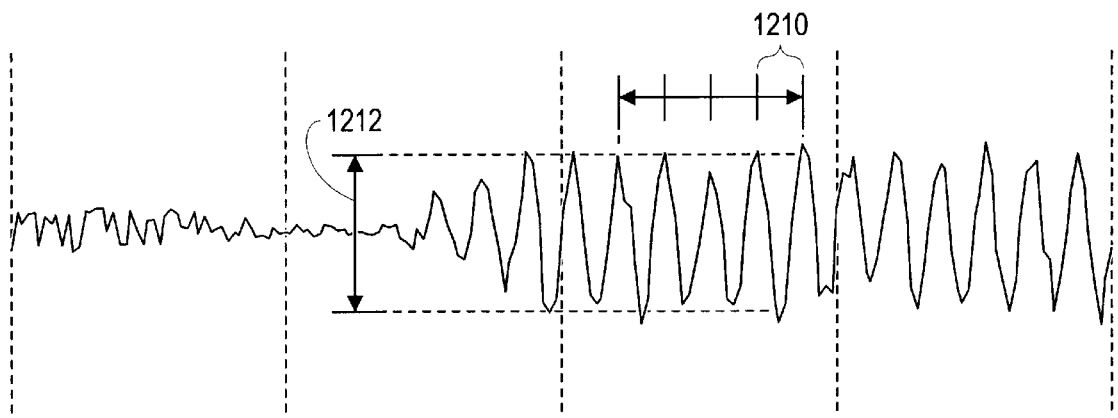
FIG. 12 is an exemplary electrographic waveform depicting the onset and first portion of a seizure, including an illustration of how a frequency characteristic is calculated according to an alternative embodiment of the invention.

FIG. 12 illustrates parameters extracted from the electrographic waveform 710 (FIG. 7) and used for adaptive stimulation in an alternative embodiment of the invention. In the seizure portion of the waveform 710, a dominant frequency or an analogous measurement can be obtained from the intervals between several successive qualified half waves obtained from the FIFO queue, especially if the electrographic waveform 710 is appropriately filtered. Specifically, dominant frequency is the inverse of the average wave duration 1210, which in turn is derived from the average interval between pairs of qualified half waves). Similarly, an average amplitude 1212 can be obtained. The expected phase of the waveform can be represented by the time the most recent qualified half wave ended plus integer multiples of the average duration —as above, the higher the number of average duration multiples used, the higher the potential for phase error.

In a preferred version of this embodiment of the invention, the number of qualified half waves taken from the FIFO queue to calculate average duration and amplitude values is a programmable number, ranging from two to eight.

Figure 13:
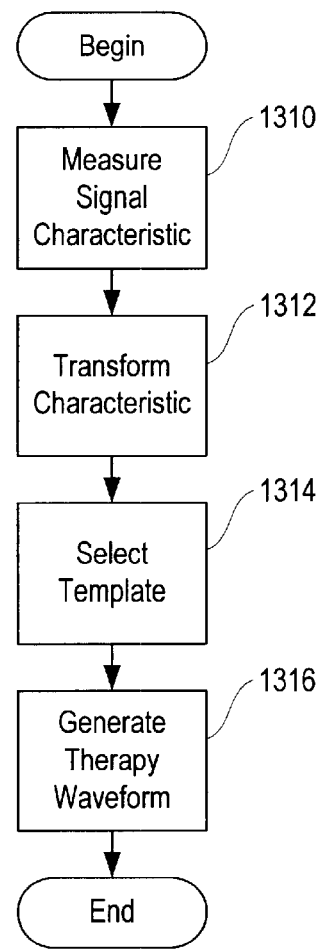
FIG. 13 is a flow chart illustrating the steps performed in generating a treatment template for adaptive electrical stimulation therapy according to the second embodiment of the invention.

The flow chart of FIG. 13 illustrates the process used to generate a treatment waveform according to the disclosed embodiment of the invention - the process of FIG. 13 can be used with the overall method set forth in FIG. 8 in place of the original embodiment of the treatment template generation process illustrated in FIG. 9.

Initially, and as graphically illustrated in FIG. 12, a signal characteristic is measured (step 1310). Examples of useful signal characteristics are dominant frequency (or average duration), average amplitude, and phase. Phase can be calculated with respect to real time (e.g. when, in real time, maxima, minima, and zero crossings are expected to occur) or in comparison to signal characteristics derived from another channel (e.g. whether one channel experiences extrema or zero crossings ahead of or behind another channel). Generally, these characteristics are continuously measured, and when an event calling for stimulation is detected, the most recent half waves (or other signal measurements) stored in the FIFO queue are used to calculate the desired characteristics.

The desired characteristic is transformed as desired (step 1312) and constrained. Exemplary transformations are described above with reference to FIG. 10; other transformations are of course possible. It is also possible to use the constraints generally described above and in connection with FIG. 10, as well as others. A stimulation template is selected (step 1314), and the therapy waveform is generated by applying the transformed and constrained characteristic to the template (step 1316), for example by defining and scheduling the start time and by defining the pulse amplitudes, inter-pulse intervals, or pulse widths, in the case of a burst of pulses.

The generated therapy signal would then be applied at the appropriate time as illustrated in FIG. 11.

Figure 14:
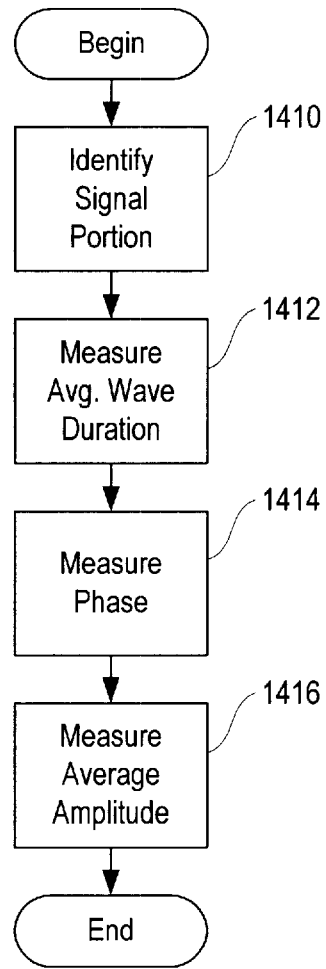
FIG. 14 is a flow chart illustrating the steps performed in extracting waveform characteristics from an electrographic signal according to the second embodiment of the invention.

Referring finally to FIG. 14, the process employed to measure signal characteristics is set forth in some detail. Initially, the desired signal portion is identified (step 1410).

Generally, the desired signal portion is represented by data in the FIFO queue when an event has been detected; it represents the most recent qualified half waves (or other signal information). A selected number of half waves (or other data samples) are identified in the FIFO queue, and a moving average duration is calculated from the qualified half wave intervals (step 1412). If desired, the moving average duration is inverted to calculate a short-term dominant frequency. Similarly, and as described above, the phase of the waveform 710 is measured by identifying the end of the most recent qualified half wave and the average duration (step 1414). The average amplitude is also calculated from a selected number of recent qualified half waves in the FIFO queue (step 1416); the number of half waves used may be the same as or different from the number used to calculate the average duration.

It should be observed that while the foregoing detailed description of various embodiments of the present invention is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to apply adaptive electrical stimulation therapy to a patient with a neurological disorder. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. A method for treating a neurological disorder in a human patient with a neurostimulator by applying electrical stimulation that is adaptive to a characteristic of an electrographic signal in the patient's brain, the method comprising the steps of:
    measuring the characteristic of the electrographic signal;
    generating a treatment waveform from the characteristic; and
    applying a stimulation signal representative of the treatment waveform.

2. The method for treating a neurological disorder of claim 1, further comprising the step of detecting a neurological event in the electrographic signal.

3. The method for treating a neurological disorder of claim 1, wherein the step of measuring the characteristic comprises the steps of:
    identifying a half wave in the electrographic signal;
    extracting a half wave parameter from the half wave;
    transforming the half wave parameter to obtain the characteristic.

4. The method for treating a neurological disorder of claim 3, wherein the half wave parameter comprises an amplitude or a duration.

5. The method for treating a neurological disorder of claim 1, wherein the step of generating a treatment waveform comprises the steps of:
    selecting a stimulation signal template; and
    transforming the stimulation signal template with the characteristic.

6. The method for treating a neurological disorder of claim 5, wherein the step of transforming the stimulation signal pattern comprises altering a duration, a frequency, an inter-pulse interval, an amplitude, or a start time of the stimulation signal template.

7. The method for treating a neurological disorder of claim 1, wherein the step of applying a stimulation signal is performed in parallel with at least one other operation performed by the neurostimulator.

8. The method for treating a neurological disorder of claim 1, wherein the step of applying a stimulation signal comprises the steps of:
    scheduling a stimulation event;
    awaiting the stimulation event; and
    delivering a stimulation signal representative of the treatment waveform.

9. The method for treating a neurological disorder of claim 1, further comprising the step of repeating the measuring, generating, and applying steps.

10. The method for treating a neurological disorder of claim 9, wherein the stimulation signal comprises a biphasic pulse.

11. The method for treating a neurological disorder of claim 1, further comprising the steps of:
    receiving the electrographic :signal with an electrode implanted in the patient's brain; and
    analyzing the signal with the neurostimulator.

12. The method for treating a neurological disorder of claim 11, wherein the step of receiving the electrographic signal is performed in parallel with at least one other operation performed by the neurostimulator.

13. A method for treating a neurological disorder in a human patient with a neurostimulator by applying an adaptive electrical stimulation signal, the method comprising the steps of:
    detecting a neurological event in a first electrographic signal;
    measuring a characteristic of a second electrographic signal;
    generating a treatment waveform from the characteristic; and
    applying a stimulation signal representative of the treatment waveform to the patient's brain.

14. The method for treating a neurological disorder of claim 13, further comprising the steps of:
    receiving the first electrographic signal from the patient's brain; and
    receiving the second electrographic signal from the patient's brain.

15. The method for treating a neurological disorder of claim 13, wherein the applying step comprises synchronizing the stimulation signal to a characteristic of a third electrographic signal.

16. The method for treating a neurological disorder of claim 15, further comprising the step of receiving the third electrographic signal from the patient's brain.

17. The method for treating a neurological disorder of claim 16, wherein the first electrographic signal is obtained from a first location, the second electrographic signal is obtained from a second location, the third electrographic signal is obtained from a third location, and the applying step comprises delivering the stimulation signal at a fourth location.

18. An implantable neurostimulator for the treatment of a neurological disorder, comprising:
    a detection subsystem adapted to detect a neurological event and to measure a characteristic of an electrographic signal;

a stimulation subsystem adapted to apply a stimulation signal to the patient's brain, wherein the stimulation signal is representative of a treatment waveform generated at least in part from the characteristic.

19. The implantable neurostimulator of claim 18, further comprising a central processing unit adapted to control the detection subsystem and the stimulation subsystem.

20. The implantable neurostimulator of claim 19, wherein the central processing unit is further adapted to transform the characteristic before the treatment waveform is generated for use by the stimulation subsystem.

21. The implantable neurostimulator of claim 18, wherein the detection subsystem is further adapted to identify a synchronization point in an electrographic signal.

22. The implantable neurostimulator of claim 21, wherein the stimulation subsystem is adapted to synchronize the stimulation signal to the synchronization point.

23. The implantable neurostimulator of claim 18, wherein the stimulation subsystem comprises a stimulation waveform generator and a stimulation signal generator.

* * * * *